Sept. 3, 1963 E. McCUMMINGS Plant Pat. 2,278
ROSE PLANT
Filed July 30, 1962
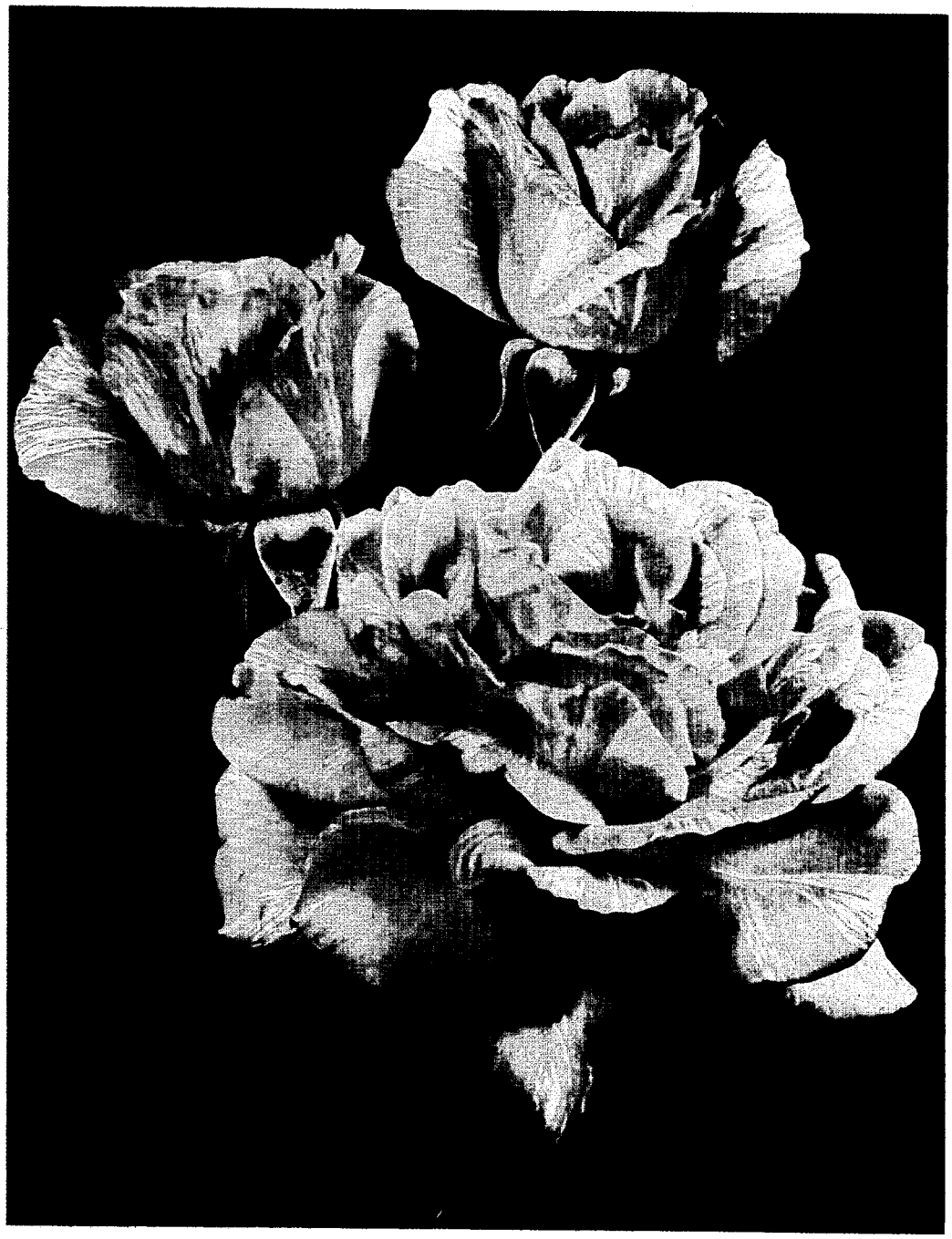
Inventor.
Edward McCummings
By: Robb & Robb
Attorneys.

United States Patent Office

Plant Pat. 2,278
Patented Sept. 3, 1963

2,278
ROSE PLANT

Edward McCummings, West Grove, Pa., assignor to The Conard-Pyle Company, West Grove, Pa., a corporation of Pennsylvania Filed July 30, 1962, Ser. No. 213,561
1 Claim. (Cl. Plt.—13)

The present invention relates to a new and distinct variety of rose plant of the hybrid tea class, which was discovered by me as a cultivated bud sport of the variety known as "Pink Peace" (Plant Patent No. 1,759).

This new variety was discovered by me during the course of my care and examination of plants being commercially grown under my supervision and direction in the fields of my assignee near West Grove, Pennsylvania. At the time of my discovery aforementioned, my attention was attracted to one particular plant which bore flowers of a color which differed from the Solferino Purple general color tonality of the flowers of the parent variety by having irregular streaks and blotches of Rhodamine Pink extending from the base of the petals to their outer margins.

Upon close inspection of this plant referred to above, I found that it had sported, and I thereupon took steps to preserve the sport and later to asexually reproduce the same. My continued observations of the original plant and the asexually reproduced progeny thereof as produced by me by budding at West Grove, Pennsylvania, fully confirmed the new flower color characteristics of the sport and conclusively established that these characteristics come true and are transmissible through succeeding propagations.

My new variety is essentially distinguished from its parent "Pink Peace," by having irregular streaks and blotches of Rhodamine Pink color extended over the surface of the petals. Other than this difference in the flower color, as noted above, my new variety is substantially identical with its parent "Pink Peace" and, accordingly, it is unnecessary to completely describe the new variety, since the features other than the flower color are substantially the same as described and illustrated in Plant Patent No. 1,759, to which reference may be had.

The accompanying drawing shows typical specimens of the flowers and foliage of my new variety in different states of development and as depicted in color as nearly true as it is reasonably possible to make the same in a color illustration of this character.

For convenience, the following is a detailed description of the flowers of my new variety, together with a brief description of the classification, plant habits and other general background details, from which the distinctions over the parent variety, as well as over all other varieties, will be apparent, with color terminology in accordance with the Horticultural Color Chart of the Royal Horticultural Society:

Type: Hardy; bush; outdoor; sport; for garden decoration.
Class: Hybrid tea.
Parentage: Sport of "Pink Peace."
Propagation: Holds its distinguishing characteristics through succeeding propagations by budding.

*Flower*

Locality where grown and observed: West Grove, Pennsylvania.
Flowers borne: Usually singly to stem; on stems of normal strength and medium length.
Quality of bloom: Free, outdoors.
Continuity: Continuous.
Bud:

*As calyx breaks.*—Color—Spinel Red, Plate 0023, with irregular markings of Spinel Pink, Plate 0625/3.

*As first petal opens.*—Color: outside—Spinel Red, Plate 0023, irregularly blotched and streaked with Dawn Pink, Plate 523/3, becoming irregularly suffused with Yellow Ochre, Plate 07/3 at base of petal, and with point of attachment Sulfur Yellow, Plate 1/1; inside—Rose Bengal, Plate 25, irregularly streaked with Rhodamine Pink, Plate 527/2, grading to Aureolin, Plate 3, at base.

This description of a newly opened flower was made from a rose grown outdoors during the month of September at West Grove, Pennsylvania:

*Color.*—Outer petal: outside surface—between Solferino Purple, Plate 26/1, and Solferino Purple, Plate 26/2, usually irregularly streaked and blotched with near Rose Pink, Plate 427/3, grading to Spinel Pink, Plate 0625/1, near base, and with point of attachment Sulfur Yellow, Plate 1/2; inside surface—Rose Bengal, Plate 25/1, with a diffuse margin of Solferino Purple, Plate 26/1, usually irregularly streaked with Rhodamine Pink, Plate 527/3, and with point of attachment Sulfur Yellow, Plate 1/2. Intermediate petal: outside surface—Spiraea Red, Plate 025/2, usually with irregular streaks and blotches of Rose Pink, Plate 427/3, and with point of attachment Sulfur Yellow, Plate 1/2; inside surface—Solferino Purple, Plate 26/1, grading to Rose Bengal, Plate 25/1, usually irregularly streaked with Rhodamine Pink, Plate 527/3, and with point of attachment Sulfur Yellow, Plate 1/2. Inner petal: outside surface—Spinel Red, Plate 0023/1, usually irregularly streaked with Magenta, Plate 27/3, and with point of attachment Sulfur Yellow, Plate 1/2; inside surface—Spiraea Red, Plate 025, usually irregularly streaked and blotched with Rhodamine Pink, Plate 527, and with point of attachment Sulfur Yellow, Plate 1/2.

This description was made from a rose that was open for three days outdoors during the month of September at West Grove, Pennsylvania.

*Color.*—Outer petal: outside surface—Solferino Purple, Plate 26/2, grading to Spinel Pink, Plate 0625/1, usually irregularly streaked with Rose Pink, Plate 427/2, and with point of attachment Sulfur Yellow, Plate 1/2; inside surface—Solferino Purple, Plate 26, usually irregularly streaked with Rhodamine Pink, Plate 527/1, and with point of attachment Sulfur Yellow, Plate 1/2. Inner petal: outside surface—Spinel Pink, Plate 0625/1, usually irregularly streaked with Rose Pink, Plate 427/2, and with point of attachment Sulfur Yellow, Plate 1/2; inside surface—Spiraea Red, Plate 025, usually irregularly streaked with Rhodamine Pink, Plate 527/1, and with point of attachment Sulfur Yellow, Plate 1/2.

*General color effect.*—Newly opened flower—Rose Bengal, Plate 25/1, with irregular streaks of Rhodamine Pink, Plate 527/3. 3 days open—Solferino Purple, Plate 26, with irregular streaks of Rhodamine Pink, Plate 527/1.

I claim:

A new and distinct variety of rose plant of the hybrid tea class, substantially as herein shown and described, characterized particularly as to novelty by being generally similar to its parent variety "Pink Peace" (Plant Patent No. 1,759), but being essentially distinguished therefrom by a Solferino Purple general color tonality of the petals, blotched and streaked in Rhodamine Pink.

No references cited.